United States Patent
Driesen et al.

(10) Patent No.: US 8,651,582 B2
(45) Date of Patent: Feb. 18, 2014

(54) METHOD FOR PRODUCING A TOOTHBRUSH HEAD

(75) Inventors: Georges Driesen, Weilrod (DE); Roland Doerr, Bad Vilbel (DE); Thorsten Koch, Schwalbach (DE); Michael Schmid, Frankfurt am Main (DE); Bernd Nootbaar, Uelversheim (DE); Michael Dümig, Kredenbach (DE); Wolfgang Schüppert, Karbach (DE); Christian Stief, Frankfurt am Main (DE); Peter Scheurich, Remlingen (DE); Roland Trombelli, Bad Soden (DE)

(73) Assignee: Braun GmbH, Kronberg (DE)

( * ) Notice: Subject to any disclaimer, the term of this patent is extended or adjusted under 35 U.S.C. 154(b) by 255 days.

(21) Appl. No.: 13/188,682

(22) Filed: Jul. 22, 2011

(65) Prior Publication Data

US 2012/0019046 A1    Jan. 26, 2012

(30) Foreign Application Priority Data

Jul. 22, 2010   (EP) .................................... 10007642

(51) Int. Cl.
*A46D 9/02* (2006.01)
*A46D 1/06* (2006.01)

(52) U.S. Cl.
USPC ............................................... 300/17; 300/21

(58) Field of Classification Search
CPC ................................... A46D 9/02; A46D 1/06
USPC ....................................................... 300/17, 21
IPC ................................................. A46D 9/02, 1/06
See application file for complete search history.

(56) References Cited

U.S. PATENT DOCUMENTS

| 3,233,943 | A | * | 2/1966 | Peterson | 300/17 |
| 3,451,173 | A | * | 6/1969 | Hazelton | 451/28 |
| 3,471,202 | A | * | 10/1969 | Lewis, Jr. | 300/2 |
| 4,831,292 | A | | 5/1989 | Berry | |
| 4,979,782 | A | * | 12/1990 | Weihrauch | 300/4 |
| 5,127,290 | A | * | 7/1992 | Warner et al. | 82/47 |
| 5,143,425 | A | * | 9/1992 | Boucherie | 300/2 |

(Continued)

FOREIGN PATENT DOCUMENTS

| DE | 12 29 495 B | 12/1966 |
| DE | 38 28 571 A1 | 3/1990 |

(Continued)

OTHER PUBLICATIONS

International Search Report for PCT/IB2011/053290, dated Nov. 29, 2011.

*Primary Examiner* — Joseph J Hail
*Assistant Examiner* — Marc Carlson
(74) *Attorney, Agent, or Firm* — John P. Colbert

(57) ABSTRACT

The present invention relates to a method for producing a brush head for a toothbrush head in which the bristle tufts that are already fixed to a bristle support of the brush head are cut at the free ends thereof such that a desired tuft end contour is generated. According to the invention, at least one bristle tuft is bent away at least in parts and held in a bent-away position while the tuft end contour of this at least one and/or of another bristle tuft is cut.

22 Claims, 12 Drawing Sheets

(56) References Cited

U.S. PATENT DOCUMENTS

| | | | | |
|---|---|---|---|---|
| 5,165,761 | A * | 11/1992 | Dirksing | 300/21 |
| 5,564,789 | A * | 10/1996 | Gerspacher | 300/21 |
| 5,593,213 | A * | 1/1997 | Meessmann | 300/21 |
| 5,683,146 | A * | 11/1997 | Falleiros et al. | 300/2 |
| 5,690,394 | A * | 11/1997 | Boucherie | 300/2 |
| 5,893,612 | A * | 4/1999 | Boucherie | 300/2 |
| 6,178,583 | B1 * | 1/2001 | Volpenhein | 15/167.1 |
| 6,290,302 | B1 * | 9/2001 | Boucherie | 300/3 |
| 6,290,303 | B1 * | 9/2001 | Boucherie | 300/5 |
| 6,808,236 | B2 * | 10/2004 | Lanvers et al. | 300/21 |
| 6,837,548 | B2 * | 1/2005 | Boucherie | 300/17 |
| 2001/0030460 | A1 * | 10/2001 | Trojanowski et al. | 300/21 |
| 2002/0109396 | A1 * | 8/2002 | Boucherie | 300/17 |
| 2002/0175557 | A1 * | 11/2002 | Motherway | 300/17 |
| 2003/0001427 | A1 * | 1/2003 | Lanvers et al. | 300/2 |
| 2004/0130221 | A1 | 7/2004 | Ichii et al. | |
| 2006/0255650 | A1 * | 11/2006 | McCarthy | 300/17 |
| 2010/0293734 | A1 * | 11/2010 | Driesen et al. | 15/167.1 |
| 2012/0174328 | A1 * | 7/2012 | Moskovich et al. | 15/106 |

FOREIGN PATENT DOCUMENTS

| | | |
|---|---|---|
| DE | 40 09 584 A1 | 10/1991 |
| DE | 195 19 291 A1 | 11/1996 |
| EP | 0 054 484 B2 | 6/1990 |
| EP | 0 444 436 A2 | 9/1991 |
| EP | 0 736 270 A1 | 10/1996 |
| EP | 0 925 740 A2 | 6/1999 |
| EP | 11 38 222 B1 | 11/2007 |
| EP | 2 186 434 A1 | 5/2010 |

* cited by examiner

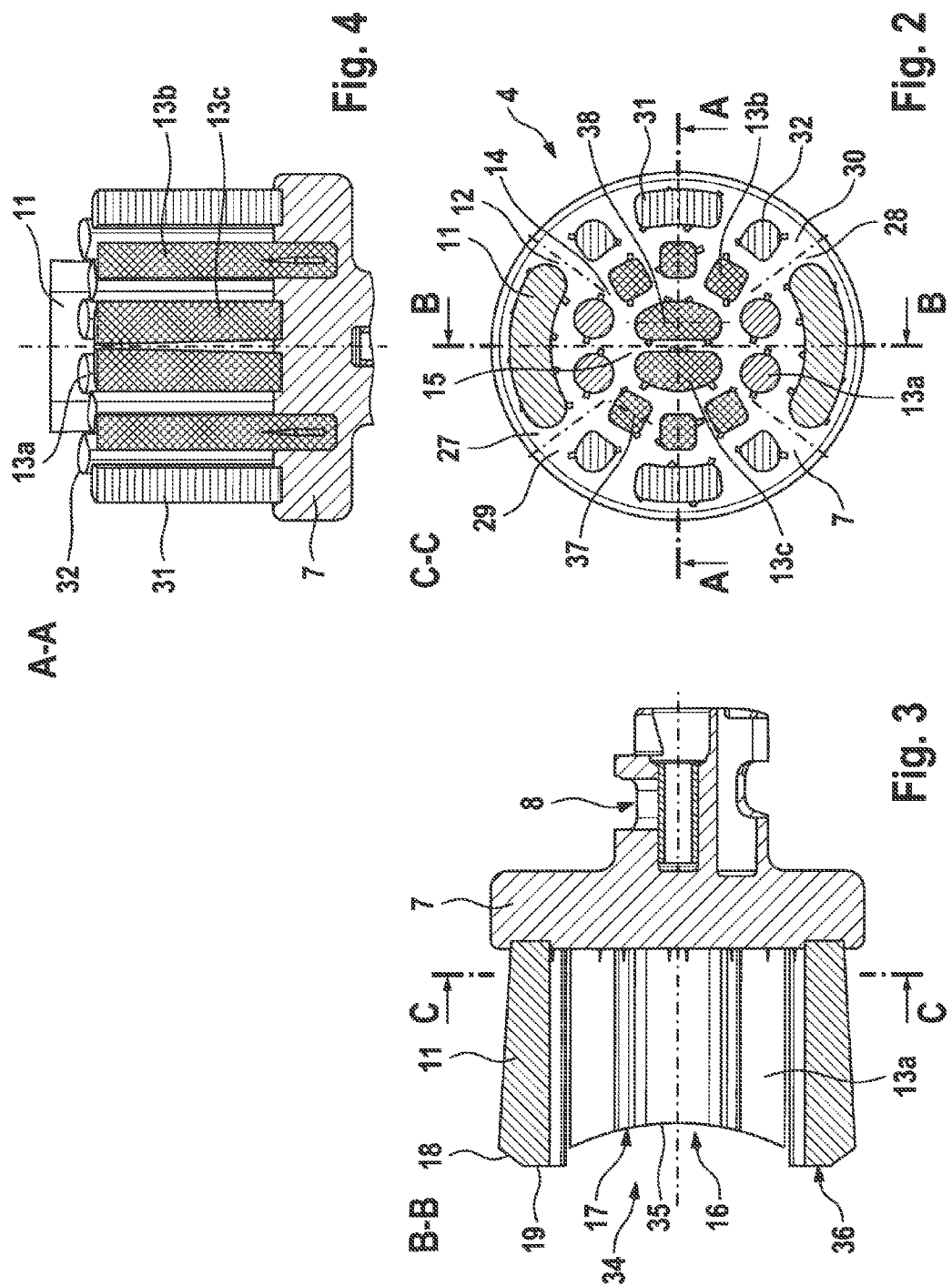

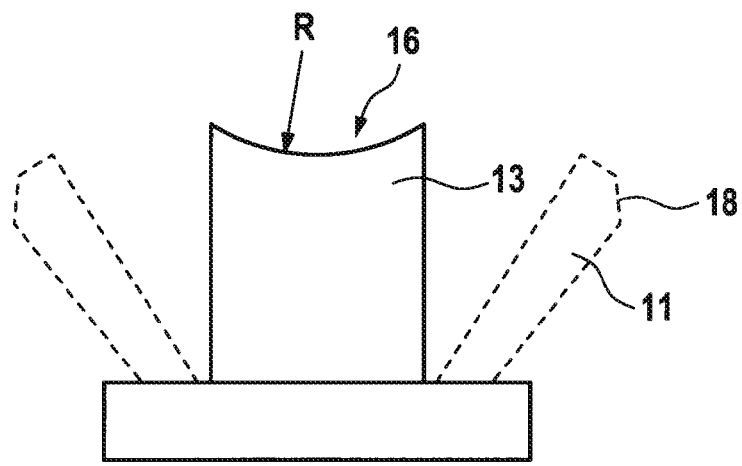
Fig. 10a
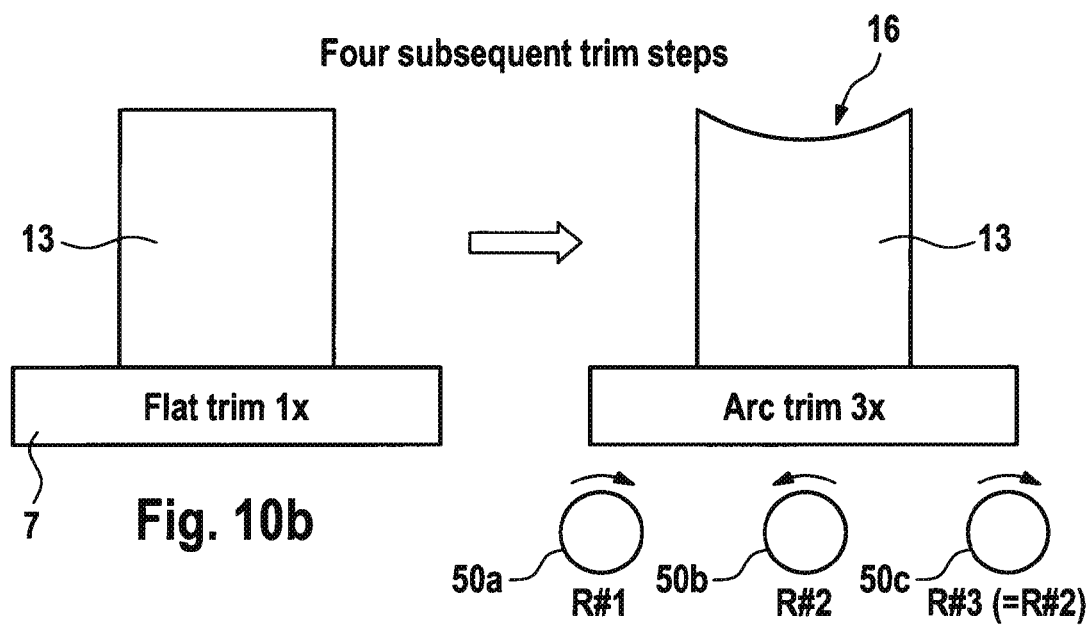
Fig. 10b
Fig. 10c

METHOD FOR PRODUCING A TOOTHBRUSH HEAD

CROSS REFERENCE TO RELATED APPLICATION

This application claims the benefit of European Patent Convention Application No. 10007642.1, filed Jul. 22, 2010, the substance of which is incorporated herein by reference in its entirety.

FIELD OF THE INVENTION

The present invention relates to a method for producing a brush head for a toothbrush head, such as a toothbrush head of an electric toothbrush, in which bristle tufts that are already fixed to a bristle support of the brush head are cut at the free ends thereof such that a desired tuft end contour is generated.

BACKGROUND OF THE INVENTION

Electric toothbrushes customarily have a bristle support that can be driven in a rotatorily oscillating manner and supports a bristle field comprising a plurality of bristle tufts, the bristle field in the overall having an approximately round, in particular circular, contour, with an oval or elliptical base area also being possible. The working surface of the bristle field in this arrangement is formed by the free ends of the bristle tufts, which can have various cross-sections. For example, in addition to the customary round bristle tufts having a circular cross-sectional area, a bristle field can also have elongated bristle tufts having an elongated, slender cross-sectional contour, or angular bristle tufts having an angular cross-sectional contour.

In order to achieve improved cleaning performance and a more pleasant brushing sensation, it has more recently been proposed to no longer design the working surface of the bristle field defined by the free ends of the bristle tufts to be flat, but to instead give the working surface a three-dimensional topography, in which some of the bristle tufts are higher than others and some of the bristle tufts have at the free ends thereof a tuft end face that is inclined toward the longitudinal axis of the bristle tuft.

In order to provide a bristle field with such three-dimensional working surfaces, the bristle tufts are trimmed accordingly, that is to say, cut at the ends thereof, so as to achieve the desired topography. Depending on the contouring of the working surface and on the cut required for this at the tuft end, this may be more or less difficult. On the one hand, the bristles tend to give way during the cutting operation, since they themselves are elastic. On the other hand, problems arise in case of dense bristle arrangements in that different bristle tufts cannot always easily be cut separately from one another, as a result of which it is not possible to achieve stepped contours.

Apart from this, in the case of angularly cut tuft ends it is often also problematic to round the bristle ends themselves in the desired manner, because the angular cut results in a bristle end that is too pointed per se, which is difficult to round or would lose too much length during the rounding process.

From DE 38 28 571 A1 a method is known for producing brushware, wherein bristle tufts are fixed to a bristle support by melting the bristles, which are made of a thermoplastic material, at the ends thereof that have been inserted into holes in the bristle support. For this purpose, the hole or hole wall of the bristle support is heated to a temperature above the melting temperature of the bristles.

From DE 195 19 291 A1 and EP 11 38 222 B1 additional methods for producing a brush head are known, in which the bristles are not fused to the bristle support, but instead are secured by means of a so-called anchor-tufting method. This is done by inserting bristle tufts, which have been folded into a U-shape, into a tuft socket in the bristle support using a metal plate that is placed between the limbs of the U-shaped bristle tuft, wherein the laterally projecting anchor plate digs itself into walls in the bristle support.

This, however, does not solve the aforementioned problems related to cutting the tuft ends.

The present invention addresses these problems by providing a method wherein it is possible to perform a cut, even of more complicated, more difficult tuft end contours, using conventional, simple cutting tools, while giving the individual bristles an easy-to-round cut contour.

This and other features, aspects, advantages, and variations of the present invention will become evident to those skilled in the art from a reading of the present disclosure with the appended claims and are covered within the scope of the claims.

SUMMARY OF THE INVENTION

The present invention relates to a method for producing a brush head for a toothbrush head. The method comprises the steps of:

a) providing bristle tufts that are fixed to a bristle support of a brush head; and b) cutting the bristle tufts at their free ends such that a tuft end contour is generated wherein at least one bristle tuft is bent away at least in part and held in a bent-away position while the tuft end contour of the at least one bristle tuft and/or of another bristle tuft is cut.

BRIEF DESCRIPTION OF THE DRAWINGS

These and other characteristics of the invention, each of which can form the subject matter of the present invention either by themselves or in subcombination irrespective of how they are combined in the claims, will be apparent not only from the claims, but also from the following description and the associated drawings, with reference to which embodiments of the invention will be explained in greater detail. In the drawings.

FIG. 2: shows a plan view of the brush head of the toothbrush of FIG. 1.

FIG. 3: shows a longitudinal section through the brush head of FIG. 2 along line B-B parallel to the longitudinal axis of the toothbrush.

FIG. 4: shows a longitudinal section through the brush head of FIG. 2 along line A-A in FIG. 2.

FIG. 10: shows a schematic illustration of the sequence of the cutting steps for cutting the groove-shaped depression in the central region of the bristle field, with partial view (a) showing the completed groove-shaped depression, partial view (b) showing the preparatory flat cut of the bristle field section to be provided with the depression, and partial view (c) showing the cutting of the depression using a plurality of rotating cutting tools having differing diameters and differing directions of rotation.

DETAILED DESCRIPTION OF THE INVENTION

Figure 1:
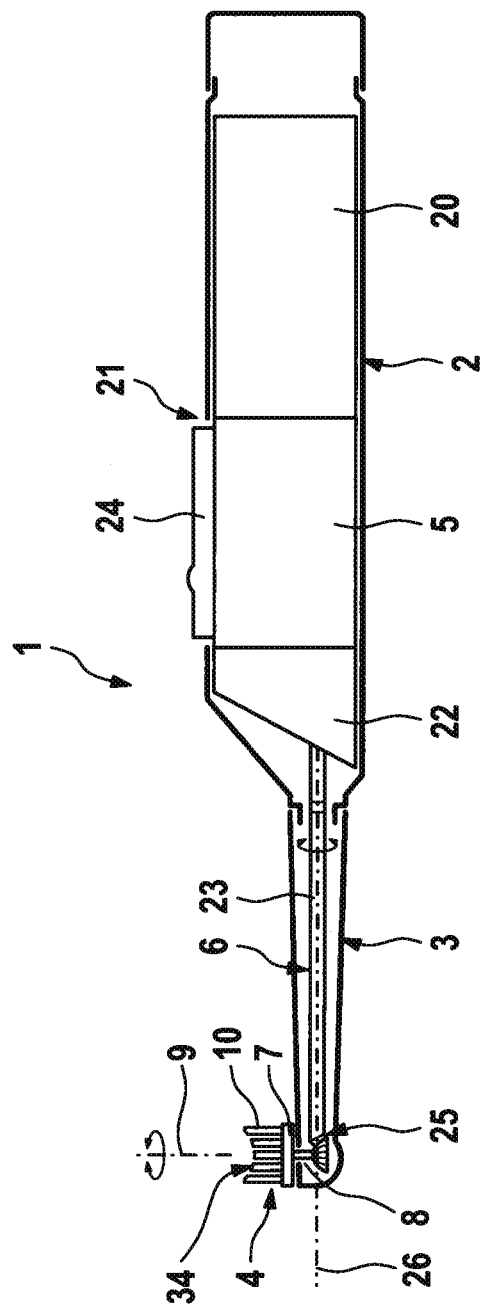
FIG. 1: shows a schematic side view of an electric toothbrush having a rotatorily drivable brush head according to one embodiment of the present invention.

Reference will now be made in detail to various embodiments of the present invention, examples of which are illustrated in the accompanying drawings.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The present invention relates to a method for producing a brush head for a toothbrush head, one non-limiting example of which is a brush head for an electric toothbrush, in which bristle tufts that are already fixed to a bristle support of the brush head are cut at the free ends thereof such that a desired tuft end contour is generated. According to the invention, at least one bristle tuft is bent away at least in parts and held in a bent-away position while the tuft end contour of this at least one and/or of another bristle tuft is cut.

In this way, the adjacent bristle field portion does not hinder the processing of the respective bristle field portion, thus enabling in particular the creation of more angular or more complicated tuft end contours, where the cutting tool, which is held in an inclined position, would otherwise cut into adjacent bristle field portions. First and foremost, however, the deflection of the bristles to be cut makes it possible to achieve other cutting geometry proportions that make more inclined and/or more curved bristle end contours possible, without cutting the ends of the individual bristles too pointed.

It is proposed to hold the bristle field against the cutting tool not in the final finished form in which it is mounted on the bristle carrier—in the natural shape thereof, so to speak—but to instead separate, deflect and selectively cut at least individual portions of the bristle field. A particular bristle field section to be cut and/or a bristle field section adjacent thereto is displaced from the neutral position thereof, in particular while elastically deforming the respective bristles in the process, and is held in the displaced position while the cut is performed. According to the invention, at least one bristle tuft is bent away at least in parts and held in a bent-away position while the tuft end contour of this at least one and/or of another bristle tuft is cut. In this way, the adjacent bristle field portion does not hinder the processing of the respective bristle field portion, thus enabling in particular also the formation of more angular or more complicated tuft end contours, where the cutting tool, which are held appropriately inclined, would otherwise cut into adjacent bristle field portions. First and foremost, however, the deflection of the bristles to be cut makes it possible to achieve different cutting geometry proportions that make more inclined and/or more arcuate bristle end contours possible, without cutting the ends of the individual bristles too pointedly.

Bending away and/or separating the respective bristle field portion or tuft portion can basically be carried out in this arrangement in various ways. In one refinement of the invention, the respective bristle group is bent into the deflected trimming position using a bending tool, which has holding means for holding the deflected bristles in the defined trimming position, so that the bristles cannot give way or give way further during the cutting operation. The bending tool in this arrangement can have at least one knife-shaped or plate-shaped engaging claw, which is slid between the bristle group to be separated and the adjacent bristle field portion, so as to bend away the bristles to be separated as required. Suitable, in particular form-fit and/or friction-fit holding means, which hold the bristles in place at the engaging claw, are provided in this arrangement on said engaging claws. For example, the holding means can have clamping means for clamping in place the bristle tuft or bristle group that is to be bent away.

Basically, various bristle tufts can be bent away and/or separated from the remaining bristle field, in order to be able to cut the separated bristle tuft itself or an adjacent bristle tuft, and optionally round the bristle ends thereof. It may be desirable in this context to bend away the longer bristle tufts, in order to be able to cut the shorter bristle tufts or to round the bristle ends thereof. Owing to the bending away of at least one bristle tuft that is longer and/or situated higher with the bristle ends thereof, access to the bristle tufts that are shorter or situated lower is made easier and the longer bristle tufts do not hinder the processing tools in advancing to the bristle tufts that are situated lower or are shorter, and the longer bristle tufts are not impacted by the processing tools moving deeper into the bristle field. The bending away of the longer bristle tufts can also be utilized to process the bent-away longer bristle tufts in a separated trimming position. It may be desirable for processing to bend away longer bristle tufts that are situated along the edge, the so-called power tips, wherein bristle tufts that are situated toward the center of the bristle field can be processed, in particular provided with a depression by means of cutting, while the outwardly situated longer bristle tufts can be held in the bent-away position.

In a refinement of the invention, the bristle end contour can be cut by means of at least one rotating cutting tool, in particular in the form of a cutter head and/or milling head, against the circumferential side of which the bristle head with the free end of the at least one bristle tuft is moved into engagement. This involves positioning the brush head in a suitable orientation substantially radially against the rotating cutting tool, so that the rotating tool with the cutting contour or cutting element thereof cuts the free end of the bristle group. Depending on how complicated the bristle field contour is that is to be cut or how many members it comprises, one or a plurality of different cutting tools may be used in the process, each of which has a blade geometry that is adapted to the bristle end contour to be cut. In particular, different contour sections can be cut in multiple cutting passes using different cutting tools, which may be one after the other, in the working surface of the bristle field, as will be explained in more detail below.

In one refinement of the invention, the bending away of at least one bristle tuft or a portion thereof can be utilized to cut a chamfer at the free end of the bristle tuft, the chamfer extending at the free end of the bristle tuft at an acute angle relative to the longitudinal axis of the bristle tuft. The chamfer can extend substantially over the entire end face of the bristle tuft; however, the chamfer is formed only over a portion of the end face of the respective bristle tuft. Depending on the design of the chamfer, only a section of the bristle tuft, or the entire bristle tuft, is bent into a trimming position displaced in a direction transverse to the tuft longitudinal axis, so that the tuft portion to be chamfered is held and cut in the bent-away trimming position.

While doing so, the bristle tuft may be desirably bent away to that side toward which said chamfer slopes. This reduces the cutting angle in relation to the angle of inclination of the chamfer in the non-deflected position, so that the bristle ends are cut off less pointed, whereby the rounding is simplified and not too much length is lost during rounding.

Cutting the chamfer in a laterally deflected tuft position, or bristle-group position, may be desirable when a more steeply designed chamfer is provided, the angle of inclination of which relative to a perpendicular end face, that is to say, a plane perpendicular to the tuft longitudinal axis, is greater than 35° and is approximately in a range of 40° to 65°, or approximately 45° to 55°. In the case of chamfers that are cut this steeply, a conventional cutting process, in which the tuft is not bent away but sits in the straight neutral position thereof, would result in excessively chamfered and very pointed bristle ends that can subsequently be rounded only with great difficulty or in reduced quality. When cutting the chamfer in a bent-away trimming position, however, the chamfer can be cut at a smaller angle of inclination, since the bristle tuft or bristle group takes on a more steeply sloping position in the region of the cut chamfer when being returned into the non-deflected neutral or desired position, that is to say a cant that is cut less steeply becomes a more steeply sloping cant. In a refinement of the invention, during cutting of the chamfer at the free end of the bent-away bristle tuft, or at the bent-away portion thereof, an angular face is therefore cut at an angle of inclination that is smaller than the desired angle of inclination of the chamfer of the non-bent bristle tuft. As a result, the bristle ends receive straighter end faces, that is to say, the inclination of the individual bristles in the region of the chamfer is less steep than the chamfer of the tuft. This allows for simple and high-quality rounding of the bristle ends, resulting in improved cleaning performance while providing a more pleasant brushing sensation and also increased wear resistance of the brush.

Depending on how steep the chamfer of the bristle tuft is to be designed, the respective bristle tuft, or the respective portion thereof, can be bent away into the trimming position to a greater or lesser degree. In a refinement of the invention, the bending angle of the bristle group between the neutral position thereof and the deflected trimming position is selected such that it corresponds—at least approximately—to the angular difference by which the desired angle of inclination of the chamfer of the tuft is greater than the angle of cut, that is to say, the angle of inclination during cutting of the bristle tuft or bristle group in the deflected trimming position. Conversely, when the bending angle cannot be freely selected, for example because the deflection during cutting cannot fall below a certain angle in order to prevent the cutting tool from colliding with an adjacent bristle field portion, the angle of inclination during cutting of the bristle tuft or bristle tuft section in the deflected trimming position can be selected smaller relative to the angle of inclination of the chamfer of the non-deflected bristle tuft by an angular difference that approximately corresponds to said bending angle.

The chamfer in this arrangement is cut by means of a flank of the rotating cutting tool, the angle of inclination of which relative to a perpendicular onto the axis of rotation of the cutting tool is smaller than the angle of inclination of the desired chamfer. In doing so, the brush head can be positioned with the axis of the bristle support thereof substantially perpendicularly against the cutting tool. The greater steepness of the chamfer of the tuft is achieved as a result of said effect that the angle of inclination increases relative to the angle that was cut when the bristles spring back into the non-deflected neutral position.

In one refinement of the invention, on the at least one bristle tuft a chamfer is cut, the angle of inclination of which relative to a perpendicular end face, that is to say a plane perpendicular to the tuft longitudinal axis, ranges between 30° and 60°, or between 35° and 55°, or between approximately 45° and 55°. The bristle field section or tuft section to be chamfered is bent away for this purpose by approximately an angle between 15° and 25° and is cut by means of a rotating cutting tool that has a cutting flank positioned at an angle of inclination of 20° to 40°, or approximately 25° to 35°, relative to the axis of rotation of the cutting tool.

In another refinement of the invention, bristle tufts situated on mutually opposing sides of the bristle field can be chamfered simultaneously. To this end, the bristle tufts, or sections thereof, situated on mutually opposing sides of the bristle field can be spread apart for cutting of the chamfers by means of a knife- and/or plate-shaped bending or spreading tool, the bent-away bristle groups being held in place by holding means in the manner described. For cutting the chamfers, a rotating cutting tool can be used, which on the circumference thereof has two cutting flanks positioned toward one another in a V-shape, against which cutting flanks the brush head with the bent-away bristle groups is held.

If the intent is to cut a straight chamfer which is designed straight in one direction, irrespective of the contour of the bristle field and/or of the bristle tuft, and which in particular forms a planar surface, the cutting tool can be moved in a straight line over the brush head or bristle groups to be cut in a direction transverse to the axis of rotation of the cutting tool. Alternatively or in addition to, the brush head can also be moved relative to the cutting tool, more specifically in the direction of the straight extension of the chamfer, which can extend parallel to the bristle support surface.

If the intent, however, is to cut a curved chamfer, which may in particular extend about the axis of rotation of the bristle field in an arcuate shape, a rotatory relative movement between the bristle field and the cutting tool is provided for in a refinement of the invention. In particular, the bristle support of the brush head to which the bristle tuft to be chamfered is fixed, and/or said bending tool with which the bristle tuft is bent away, can be turned about the axis of rotation of the bristle support while the chamfer at the free end of the bristle tuft is cut.

Alternatively or in addition to cutting a chamfer, in a refinement of the invention a depression having a groove-shaped bottom, which is curved in an arcuate manner in one direction and straight in a direction perpendicular thereto, can be cut notably in a central section of the bristle field or working surface thereof. Such a central indentation in a bristle field may be desirable for various reasons, for example a tooth cleaning agent, such as toothpaste for example, is held better on the working surface, and in the case of bristle fields driven in a rotatory manner an improved centering effect on the respective tooth to be cleaned is achieved, and at the same time the tooth flank is hugged in an improved manner, as a result of which in particular also the edges of a tooth flank toward the interproximal spaces are brushed better.

Such a groove-shaped depression in the central region of the bristle field or the working surface thereof is advantageously likewise cut by means of a rotating cutting knife, which on the circumference thereof has a similarly convexly curved cutting contour, against which the bristle field is held with the free ends of the bristle tufts. An adjacent bristle field section, in particular oppositely situated bristle tufts situated along the edge that are intended to have a raised contour relative to the central region, is bent away to the side such that same cannot come into engagement with the cutting contour of the knife working out the groove-shaped depression.

Cutting the groove-shaped depression may be carried out in multiple process steps, wherein the corresponding bristle field section is cut consecutively using a plurality of rotating cutting tools having differing diameters and/or differing directions of rotation. In particular, it is possible to first use a rotating cutting tool that has a larger diameter or larger radius, in order to cut a kind of preliminary depression into the respective bristle field section, before a further cutting tool that has a smaller diameter or radius as compared to the aforementioned cutting tool is used to cut the depression further, or to cut a further preliminary depression, which can optionally be cut in a third or further pass using optionally further cutting tools having an even smaller diameter or radius and/or an opposite direction of rotation.

A cutting operation using a plurality of cutting tools having decreasing diameters allows the dimensional accuracy of the groove-shaped depression to be improved. This makes it possible in particular to counter the effect that the section of the bristle field to be provided with the groove-shaped depression, which section is cut first by the cutting tool or in which the cutting tool enters into said bristle field section, is given a radius that is too small or a radius smaller than that of the bristle field section in which the cutting tool moves out of the bristle field. This effect can occur in particular when the groove-shaped depression is cut in a single pass using a single cutting tool.

In order to further improve the dimensional accuracy, the bristle field section into which said groove-shaped depression is to be introduced, can first be cut flat in a preparatory process step before the groove-shaped depression is cut into same in a further process step or in a plurality of further process steps. In particular, the flat and/or level cut of said bristle field section can be effected at a height that substantially corresponds to the highest contour section of the desired groove-shaped depression. The flat cut can take place in particular at approximately the height at which the bristles are supposed have the bristle ends thereof that define the highest part of the groove-shaped contour. Such a flat cut prior to cutting the concave depression reduces the degree of asymmetries that may occur while cutting the concave depression.

The process of cutting the concave depressions in the bristle fields in a plurality of process steps using a plurality of rotating cutting knives having differing diameters and/or differing directions of rotation, and/or including a preparatory flat or level preliminary cut can improve the dimensional accuracy of the desired depression in a desirable manner optionally without the above-explained bending away of bristle tufts, however, provision can also be made to bend away the bristle tufts adjacent to or bordering the depression and/or in particular bristle tufts situated along the edge, so as to have free access to the bristle field sections to be provided with the depression.

Alternatively or in addition to the bending away of bristle tufts, it is also possible according to the invention to initially anchor not all of the bristle tufts to the bristle support, but to instead successively anchor individual bristle tufts to the bristle support and to cut them, and optionally to round same at the bristle ends thereof. In particular, initially at least one bristle tuft can be anchored to the bristle support and then cut in the manner described, before at least one further bristle tuft is anchored to the bristle support in a later process step.

The order of the bristle tufts to be anchored and cut can basically be varied in such a successive anchoring and cutting operation. According to one refinement of the invention, it is possible in particular to first anchor, cut and optionally round at the bristle ends bristle tufts that are shorter or have lower-lying free ends, before at least one longer bristle tuft is anchored to the bristle support and then cut and optionally also rounded at the bristle ends. Owing to the selective anchoring of initially only shorter bristle tufts, these can be processed in terms of the contour and free ends thereof without impairment by the longer bristle tufts. The longer bristle tufts that are subsequently fixed to the bristle support, in turn, can be cut and optionally rounded unhindered by the shorter bristle tufts, the processing of which has already been completed, since the shorter bristle tufts that are situated lower with the free ends thereof do not collide with the tools that are moved into a higher processing plane.

In another refinement of the invention, the bristle ends are rounded after the tuft end contours have been cut, so as to achieve a more pleasant brushing sensation and prevent micro injuries to the gums. Moreover, the bristles become more wear-resistant in the process.

In a refinement of the invention, rounding of the bristle ends can be carried out in multiple process steps using different processing tools. In particular, a coarser grinding tool can be used for a preliminary processing operation and a finer grinding or polishing tool can then be used for finishing.

In a refinement of the invention, a rotating grinding tool, which is provided on a surface thereof with a suitable grinding layer and that may have various designs with respect to the shape thereof and be adapted to the particular grinding task, can be used for rounding the bristle ends.

According to a refinement of the invention, the bristle ends can be rounded using a rotating grinding roller that is moved with the circumferential side thereof into engagement with the bristle ends and, in addition to the rotating movement thereof, is moved relative to the bristles. In particular, said grinding roller can be moved translationally in a plane parallel to the axis of rotation of the grinding roller and/or parallel to the bristle field surface, the bristles of which are to be processed, in particular parallel to the axis of rotation and/or perpendicular thereto. Alternatively or in addition, the grinding roller can also be turned about an axis perpendicular to the axis of rotation thereof, which may be substantially parallel to the longitudinal axis of the bristles to be rounded. As a result of such additional movements, more even rounding of the bristle ends can be achieved. Said additional movements can be performed directly by said grinding roll. Alternatively or in addition, however, the additional movements can also be generated by moving the bristle field relative to the grinding roll.

Alternatively or in addition to such a grinding roll, the bristle ends can also be rounded by means of a rotating grinding wheel that is moved with a flat or end face into engagement with the bristle ends to be rounded. Such a grinding wheel, in addition to the rotating movement thereof, is also moved relative to the bristle ends, more specifically in a plane substantially perpendicular to the axis of rotation of the grinding wheel. The additional movements can be of a translational nature, for example moving back and forth along an axis or moving back and forth in an alternating manner relative to two axes. In particular, the grinding wheel can also be moved along an orbit about the axis of rotation of the grinding wheel relative to the bristle ends. As a result of such additional movements of the grinding wheel, more even rounding of the bristle ends can be achieved.

With such a grinding wheel as well, said additional movements can be generated directly by the grinding wheel and/or by appropriately moving the bristle field relative to the grinding wheel.

The bristle tufts may be isolated from adjacent bristle tufts when rounding the bristle ends of the bristle tufts, for example by bending away the bristle tuft to be processed and/or an adjacent bristle tuft, substantially analogously to the aforedescribed separating of the bristle tufts for the purpose of cutting the same.

The sequence of cutting and rounding the bristle tufts can be useful in various ways. According to an embodiment of the invention, it is possible to first cut all of the bristle tufts that are to be cut, before finishing of the bristle tufts, in particular grinding and/or polishing or rounding of the bristle ends is performed in some other way.

Alternatively, it can be useful with certain bristle field configurations to initially not only cut but also immediately finish at least one bristle tuft, subjecting the same in particular to a grinding, polishing or rounding step in some other way, before another bristle tuft is cut and optionally likewise finished. According to a refinement of the invention, notably first the bristle tufts having a shorter length are cut, ground, polished or rounded in some other way, before bristle tufts having a longer length are cut, ground, polished, or rounded at the bristle ends in some other way. Alternatively, longer bristle tufts can first be cut, ground, polished, and/or rounded in some other way at the bristle ends before bristle tufts having a shorter length are cut and finished in a corresponding manner.

The toothbrush 1 shown in FIG. 1 comprises a handpiece 2 and a brush head 4 that can be coupled thereto. More specifically, the brush head 4 can be coupled to a neck 3 of the toothbrush 1 that is connected to the handpiece 2 and designed in the form of a hollow brush tube. However, it would also be possible for the brush head 4 to comprise said neck 3, or at least a portion thereof, and for it to be couplable along with the same to the handpiece 2.

The handpiece 2 accommodates in the interior thereof an energy storage device 20, which may be in the form of a rechargeable battery; a motor 5 (such as in the form of an electric motor); and a control unit 21.

In the embodiment shown, the rotary motion of the motor 5 is translated via a gear mechanism 22 into a rotatorily oscillating movement of a drive shaft 23 that extends through the neck 3 to the brush head 4. The toothbrush 1 can be activated and deactivated via a switch 24 mounted on the handpiece 2.

In the embodiment shown, the brush head 4 is caused to perform an oscillating rotational motion about an axis of rotation 9 via a bevel gear step 25 at the end of the drive shaft 23, said axis of rotation extending substantially transversely to the toothbrush longitudinal axis 26.

An embodiment of the brush head 4 of the toothbrush 1 is shown in FIGS. 2 to 5. The bristle support 7 is designed round, however, not circular but slightly oval and/or elliptical, the longer axis of the oval or of the ellipse in the neutral position of the bristle support 7 extending parallel to the toothbrush longitudinal axis 26, and the shorter axis of the oval or of the ellipse extending in a direction transverse thereto. In FIG. 2 the longer axis of the oval or of the ellipse is parallel to the line B-B.

Arranged on the bristle support 7 is a plurality of bristle tufts, which are arranged in a plurality of rings 12, 14 and 15 and distributed over the bristle field 10. Positioned on an outer ring 12 in the embodiment shown according to FIG. 2 are eight bristle tufts, four of which have an elongated contour, while another four have a—roughly speaking—round or equilateral cross-sectional contour. The length of the bristle tufts on said outer ring 12 varies in this arrangement, as will be explained in more detail later, with longer bristle tufts generally being provided—roughly speaking—in mutually opposing sectors 27 and 28, which in the initial position of the bristle support 7 contain the toothbrush longitudinal axis 26, than in sectors 29 and 30 are oriented in a direction transverse thereto or situated in between; see FIG. 2.

As shown in FIG. 2, the bristle tufts 11 and 31 of the outer ring 12 that are situated on the major axes B-B and A-A, respectively, are designed elongated in the plan view, whereas the bristle tufts 32 situated in between have an approximately equilateral contour or an approximately cubic or round cross-section. Said elongated bristle tufts 11 and 31 both extend in an arcuate curve around the axis of rotation 9, see FIG. 2.

The outer bristle tufts 11 situated on the longer major axis B-B extend over a circumferential section of approximately 50° to 90°, or approximately 70°, whereas the outer bristle tufts 31 situated on the shorter major axis A-A extend over a circumferential section of approximately 20° to 45°, or approximately 30°.

Positioned on a second ring 15 of bristle tufts, as viewed from the outside, are altogether 10 bristle tufts 13a and 13b, of which some have a circular cross-section and others an angular cross-section. In particular, tufts 13a having a circular cross-section are arranged, as shown in FIG. 2, in sectors 27 and 28 in which the longer outer tufts 11 of the outer ring 12 are situated, while angular bristle tufts are provided in sectors 29 and 30 of the bristle support 7 that are situated therebetween, on the second ring 14. The length of these bristle tufts 13a and 13b on the second ring 14 also cyclically varies from tuft to tuft along the circumference of the ring 14, more specifically such that longer bristle tufts are provided in said sectors 27 and 28 than in the sectors 29 and 30 situated on the shorter major axis.

Lastly, in an innermost region or in a third ring of tufts, as viewed from the outside, two elongated bristle tufts 13c are provided, which each extend with the longitudinal extent thereof in a direction parallel to the longer major axis B-B.

As FIG. 3 shows, the bristle tufts of the bristle field 10 are contoured at the free ends thereof, or matched to each other in terms of the length and/or height thereof, in such a way that the working surface 34 of the bristle field 10 defined by the free ends of the bristle tufts has a central depression 16, which has a groove-shaped bottom 17 extending in an arcuate shape in one direction and straight in a direction perpendicular thereto. The curvature extends in the direction of the longer major axis B-B, or in the direction of the toothbrush longitudinal axis 26 when the bristle support 7 is in the non-deflected neutral position thereof. In a direction perpendicular thereto, which extends parallel to the shorter major axis A-A of the bristle support 7 and/or transversely to the toothbrush longitudinal axis 26 when the bristle support 7 is in the non-deflected neutral position thereof, the depression 16 has a straight contouring, as shown in FIG. 3.

The central depression 16 can be designed to be variously deep. In a refinement of the invention, the lowest point of the depression 16 is set deeper relative to the highest point of the bristle field 10 by an amount of approximately 1 mm to 3 mm, or approximately 2 mm. The groove-shaped contouring of the bottom 17 of the depression 16 can basically be variously curved in this arrangement. In the embodiment shown in FIGS. 3 to 5, a circular arc-shaped contouring having a radius of curvature in a range of 7.5 mm to 15 mm, or approximately 10 mm, is provided, but this can vary depending on the dimensioning and configuration of the bristle field.

The working surface 34 of the bristle field 10 that is formed by the free ends of the bristles can be positioned angularly, that is, it does not extend parallel to the surface of the bristle support 7. The angle of slope of said working surface 34 relative to the perpendicular onto the bristle field major axis 46 in this arrangement is approximately 3.5°+/−1°. Since said working surface 34 is not designed planar but includes a groove-shaped curved depression in the aforementioned manner, and since the bristle tufts situated along the edge protrude, said slope refers to the slope of a plane which is placed approximately over the working surface and which may be determined, for example, by the highest points of the working surface and/or by statistical averaging of the sectional slopes. To this end, the groove-shaped depression 16 can be designed "askew", in particular curved in a banana shape, and the outer bristle tufts 11 projecting in terms of height can have differing heights.

As FIG. 3 shows, the end faces of the inner tufts 13a, 13b and 13c and the end faces of the shorter, outer tufts 31, which likewise contribute to defining the groove-shaped bottom 17, are designed not as plane surfaces, but are likewise in themselves curved in a groove-shape. The end faces 35 curved in a groove-shaped manner complement each other and together form said groove-shaped contour of the bottom 17 of the central depression 16. Specifically, the slope of the end faces of the inner bristle tufts 13 increases as the distance from the axis of rotation 9 in the direction parallel to the major axis B-B increases; see FIG. 3. In other words: the bristle tufts arranged on the major axis A-A extending in a direction transverse to the axis B-B are slightly curved at the free ends thereof, but nevertheless are aligned substantially parallel to the bristle support surface, while the slope of the free ends increases as the distance from said major axis A-A increases.

As FIG. 3 also shows, the outer tufts 11 of the outer ring 12 that are arranged in the sectors 27 and 28 are extended in length relative to the remaining bristle tufts or have a greater height, so that they protrude beyond the remaining bristle tufts. This also results in a step in height relative to the central depression 16, see FIG. 3; that is, the central depression 16 in the embodiment shown in FIG. 3 does not transition continuously into the end faces of said outer tufts 11.

The outer tufts 11 in the mutually opposing sectors 27 and 28, which in the neutral position of the bristle support contain the toothbrush longitudinal axis 26, have end faces 36 that comprise a flat section 19, which is aligned substantially perpendicularly to the longitudinal axis of the bristle tufts 11, as well as chamfers 18, which taper said end faces 36 toward the outside.

Figure 5:
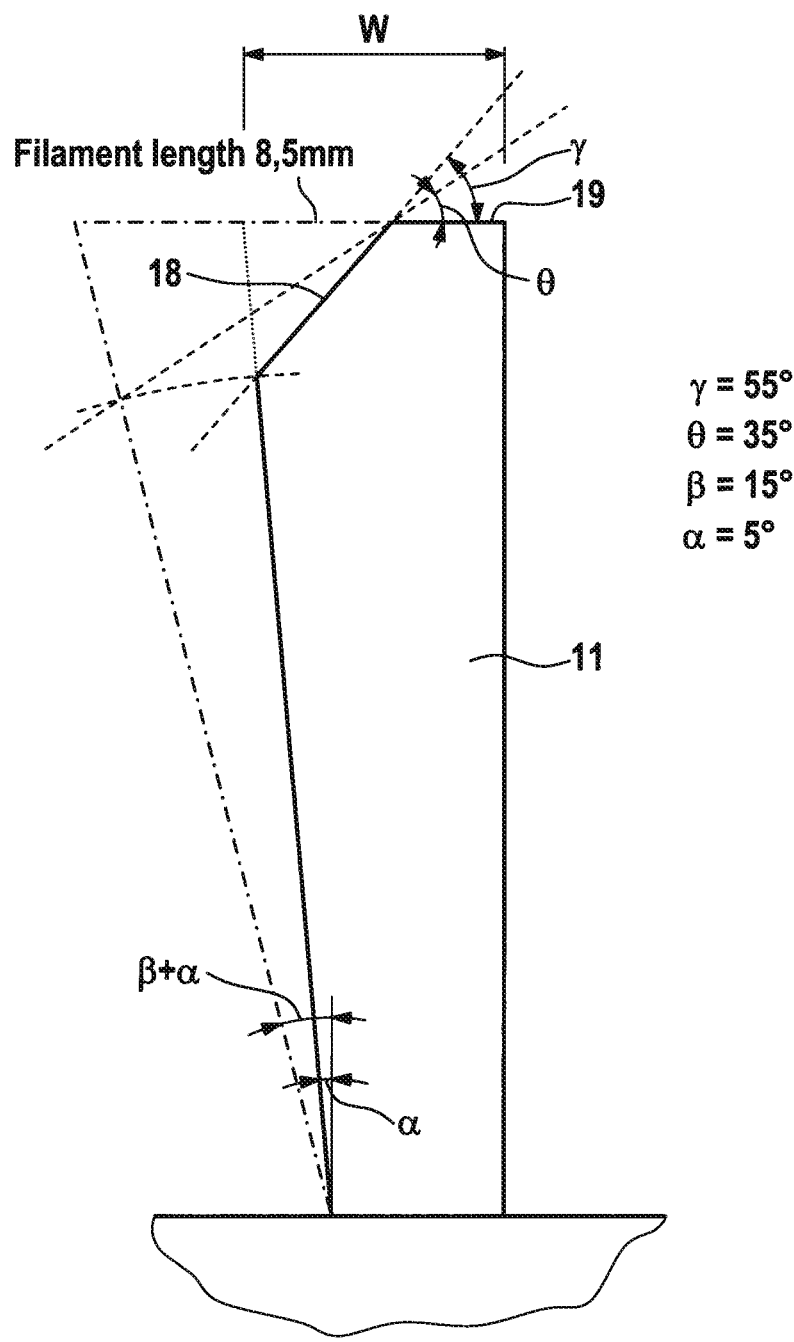
FIG. 5: shows an enlarged side view of one of the outer, longer bristle tufts of FIG. 3 in an enlarged, schematic illustration showing the angular proportions of the chamfer of the tuft.

As FIG. 5 shows, said chamfers 18 in this arrangement extend at an angle γ in a range of 20° to 60°, or approximately 35° to 55°, and in the embodiment shown at approximately 55°. The chamfers 18 are designed so deep and wide as to extend over approximately 25° to 75° of the width W of the respective bristle tuft 11. The width W in this context refers to the extension of the bristle tuft perpendicular to the longitudinal axis of the bristle tuft and perpendicular to the longitudinal extension of the chamfer 18, specifically in the region of the free end of the bristle tuft; see FIG. 5. In the embodiment shown in FIG. 5, the chamfer thus extends over approximately ⅓ to ⅔ of the width W.

Said longer outer bristle tufts 11 in this arrangement are designed in the overall in a trapezoidal manner, as viewed in the longitudinal section thereof. While the inner flank of the respective bristle tuft 11 extends substantially perpendicularly to the plane defined by the bristle support 7, the outer flank is inclined at an angle α of approximately 3° to 10°, or approximately 5°, to a perpendicular onto the bristle support 7, so that the cross-section of the bristle tuft 11 increases toward the free end thereof, that is to say, the bristle tuft becomes wider toward the free end. In this way, a large working surface can be achieved with the given limited size of the bristle support 7. Moreover, favorable geometrical proportions result at the free end of the bristle tuft 11 in terms of the chamfer 18 thereof.

In order to hug the tooth flanks as extensively as possible, distribute the brushing pressure over a large surface area and hold toothpaste or the like on the working surface 34, the bristle tufts occupy with the free ends thereof at least 50% of the area defined by the bristle support 7, or even ⅔ or more thereof. As FIG. 2 shows, the bristle tufts on the outer ring 12 can extend over a circumferential section of approximately 200° to 300°. with the extent of all of the bristle tufts being added together. The second ring 14 of bristle tufts, as viewed from the outside, can extend over a circumference of altogether likewise approximately 200° to 300°, with the extent of all of the bristle tufts along the circumference being added together. The free ends of the innermost bristle tufts can cover an area that is continuous substantially over the entire surface thereof.

Cutting the bristle tufts in order to achieve the topography described takes place in this arrangement in the manner apparent from FIGS. 5 to 8.

As FIG. 8 illustrates, in this embodiment all of the bristle tufts are first anchored to the bristle support 7, which can be carried out, for example, by means of an anchor tufting method.

Alternatively, it is also possible that initially only some of the bristle tufts or only at least one bristle tuft are/is anchored to the bristle support, in order to cut and optionally finish this portion of bristle tufts, or this at least one bristle tuft, before additional bristle tufts are anchored to the bristle support, as was already explained in greater detail at the beginning.

All of the bristle tufts are then initially cut to an even level in a manner known per se, as shown in FIG. 8 (a).

Then one of the longer bristle tufts 11 is shortened to a shorter length, as is shown in FIG. 8 (b) and as is required in order to achieve the aforedescribed asymmetric topography.

Then the outer, elongated and raised bristle tufts 11 are provided with the chamfers 18, as will be explained further below, according to the process steps illustrated in FIGS. 8 (c) and 8 (d). Lastly, the central, groove-shaped depression 16 is cut into the working surface 34 of the bristle field 10 as shown in FIG. 8 (e).

Figure 6:
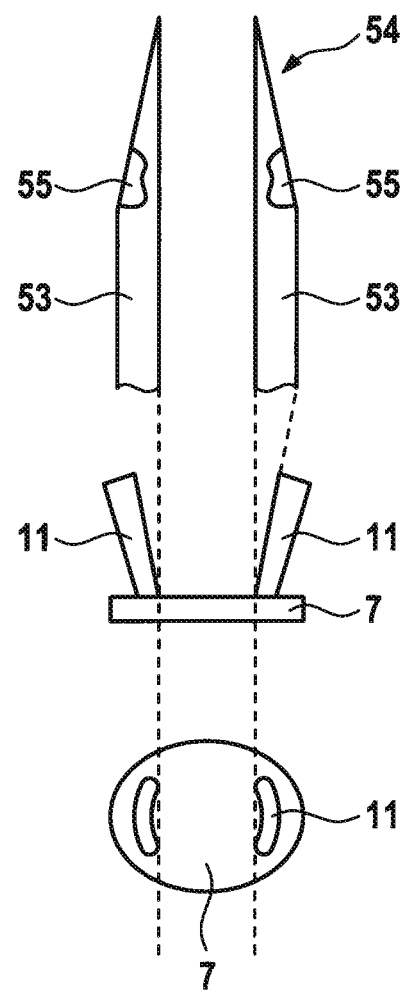
FIG. 6: shows a schematic side view of the bending tool for deflecting individual bristle groups into a trimming position in which the bristle end contour is cut.
Figure 7:
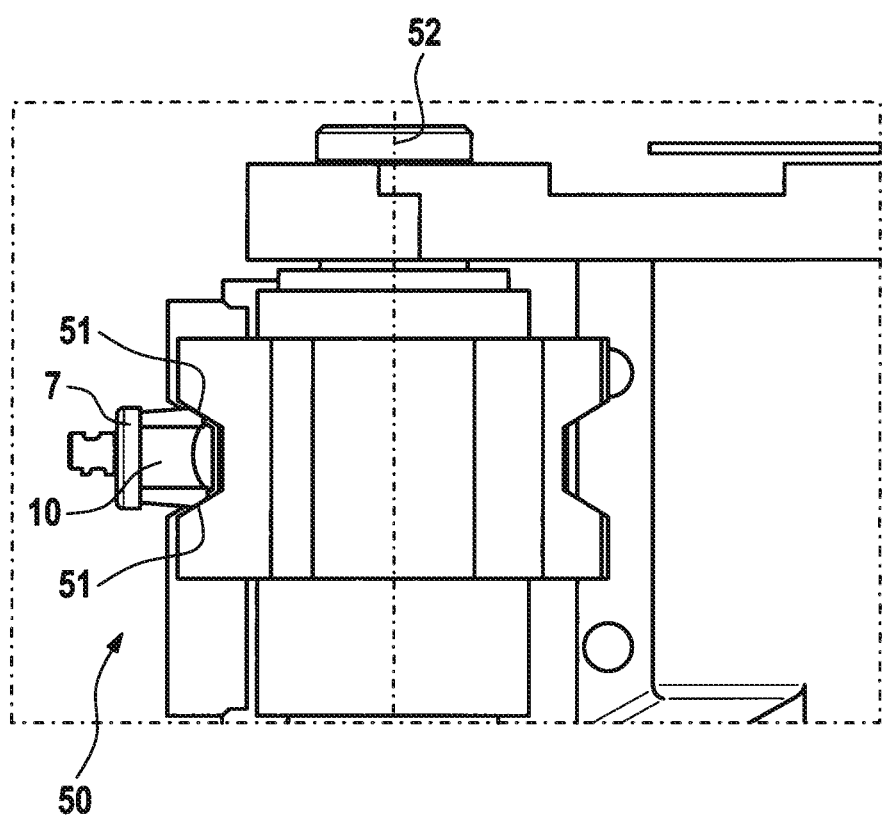
FIG. 7: shows a schematic side view of a rotating cutting tool for cutting the tuft end contour.
Figure 8A:
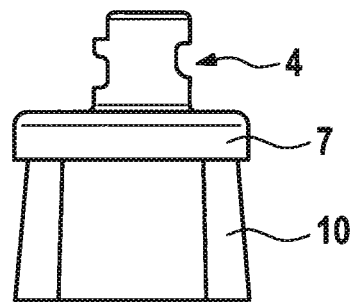
FIG. 8: shows a schematic flow diagram for illustration of the sequence of the multiple trimming steps, showing the brush head in a schematic side view in each case after various cutting steps.
Figure 8B:
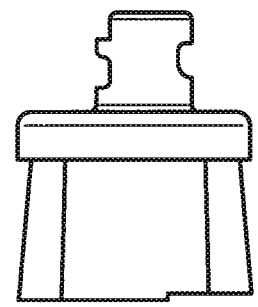
Figure 8C:
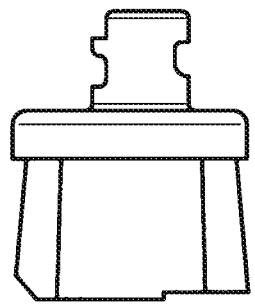
Figure 8D:
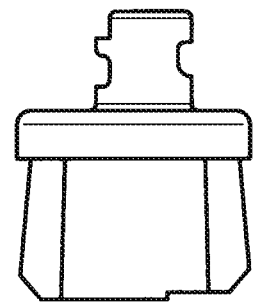
Figure 8E:
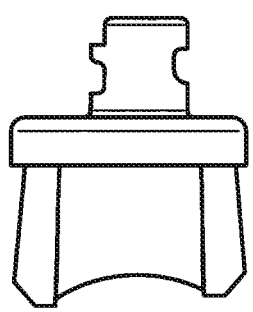
Figure 9A:
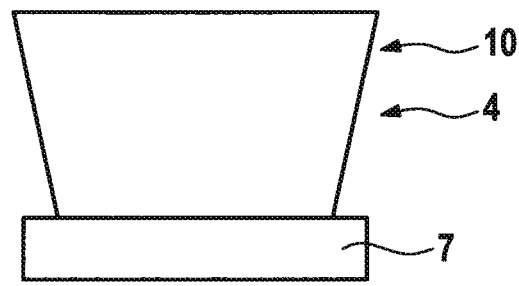
FIG. 9: shows a schematic illustration of the trimming steps according to an embodiment of the invention similar to FIG. 8, with partial views (a) to (j) illustrating the brush head and the bristle field thereof in different cutting and finishing stages, as well as the grinding tools used for the finishing steps and the movements thereof.
Figure 9B:
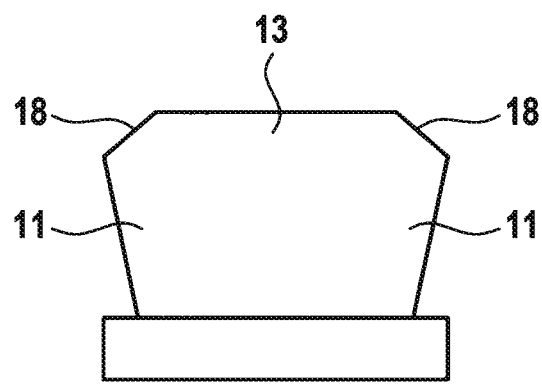
Figure 9C:
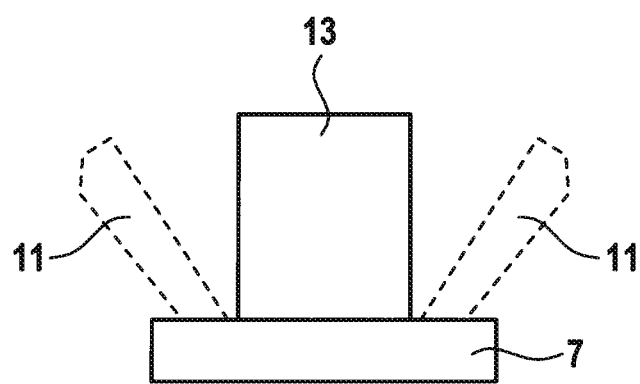
Figure 9D:
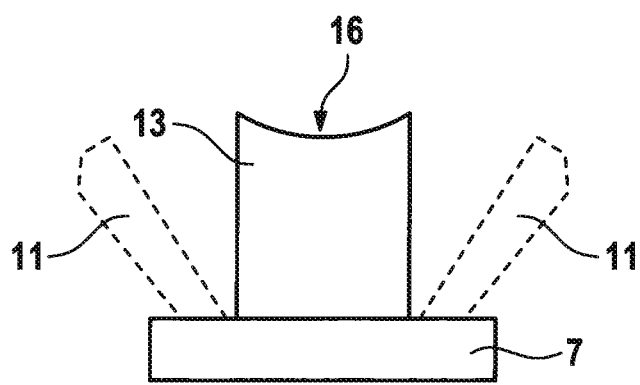
Figure 9E:
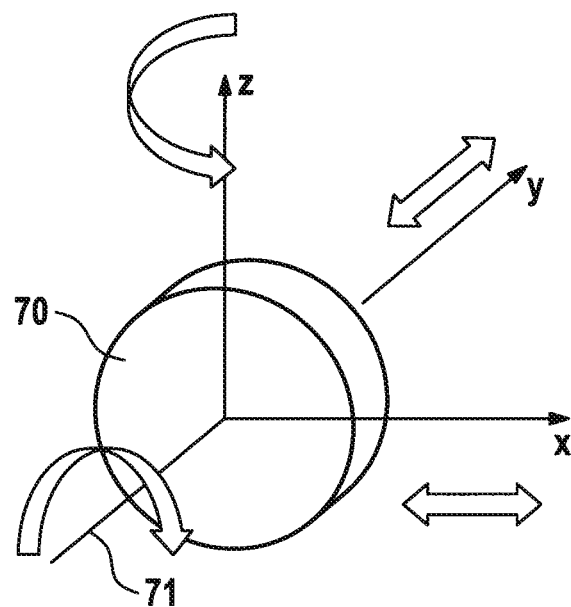
Figure 9F:
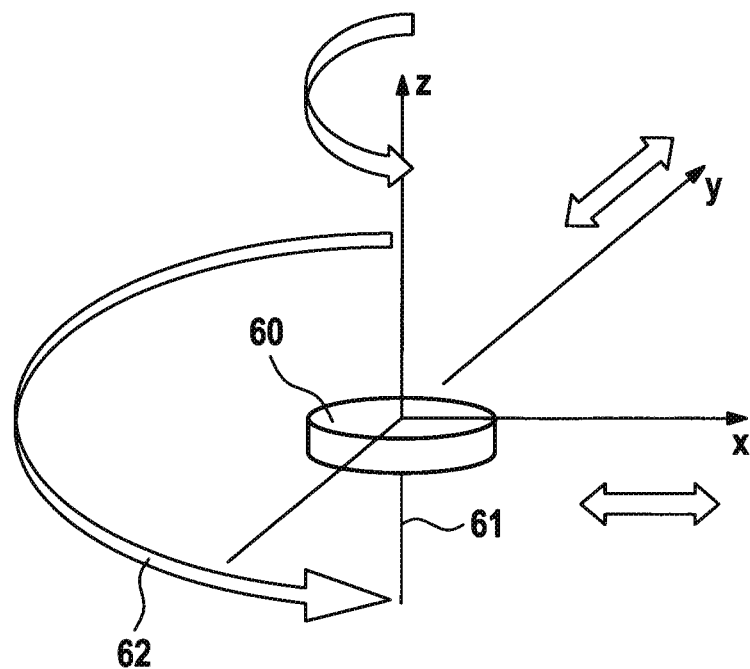
Figure 9G:
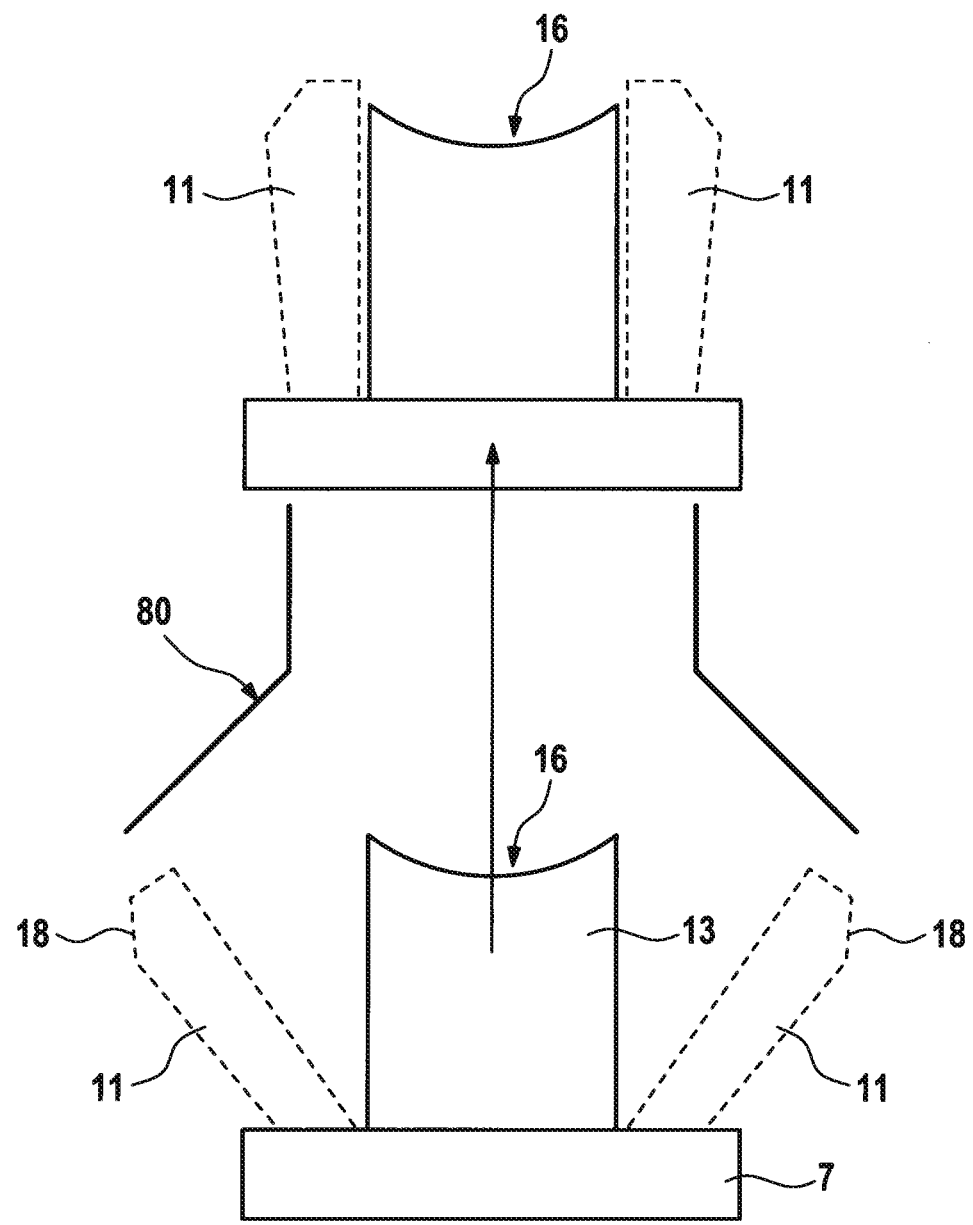
Figure 9H:
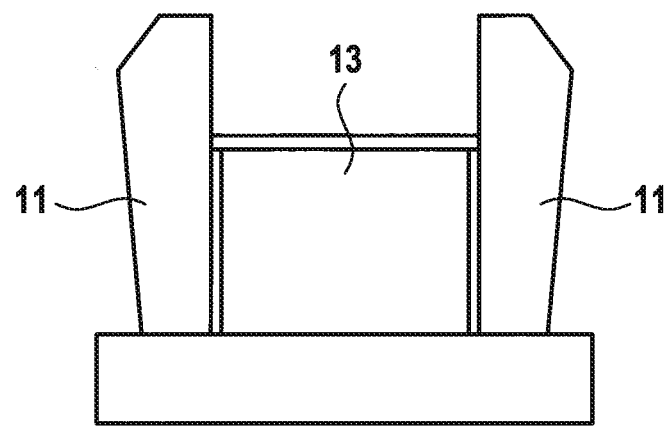
Figure 9I:
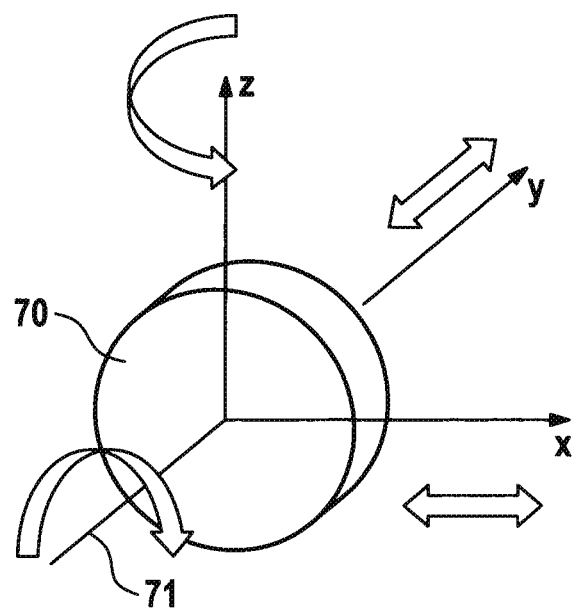
Figure 9J:
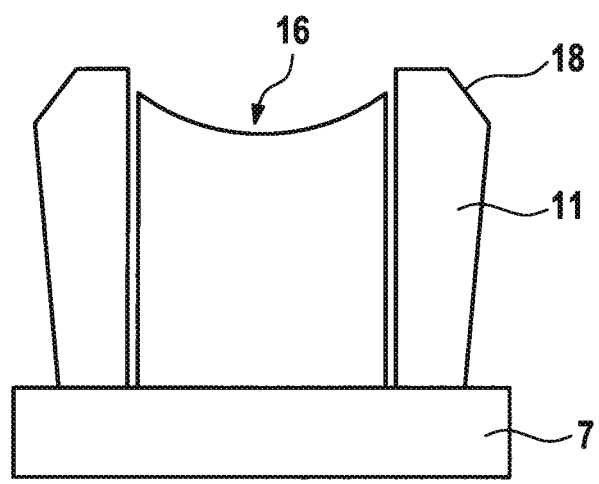

As is illustrated in FIGS. 5 and 6, for cutting the chamfers 18, the outer bristle tufts 11, or the sections thereof to be chamfered, are bent away to the side in each case by means of a bending device 54 in order to be able to cut the chamfer 18 at a less steep angle of inclination. As is shown in FIG. 7, the bending device 54 comprises two knife- or plate-shaped bending claws 53, by means of which the bristle groups to be cut can be separated and bent away to the side. Suitable holding means 55 are provided for that purpose on said engaging claws 53, for example in the form of clamping means, so as to be able to hold the bent-away bristle groups in the bent-away trimming position.

As is shown in FIG. 5, the corresponding bristle group of a bristle 11, on which a chamfer 18 having an angle of inclination γ in the range of 45° to 55° is to be provided, is bent away toward the outside by a bending angle β of approximately 15°, whereby the free ends move toward the outside in the manner illustrated by the dashed lines in FIG. 5.

In this outwardly bent trimming position, the bristle groups to be chamfered are then held against the circumferential side of a rotating cutting tool 50 in the form of a cutter head or milling head, as is shown schematically in FIG. 7. Said cutting tool 50 has a trapezoidally contoured circumference side, or cutting edges 51 that are positioned trapezoidally in relation to one another, the positioning angle of which relative to the axis of rotation 52 is less steep than the desired angle of inclination of the chamfers 18. In particular, said cutting edges 51 can be inclined at an angle θ of only 20° to 35°.

If straight chamfers 18 are to be cut that extend in a straight direction transversely to the axis of rotation of the bristle field 10, irrespective of the arcuate contouring of the bristle tufts 11, the cutting tool 50 is moved transversely over the brush head 4 in the corresponding direction or, conversely the brush head 4 is moved relative to the cutting tool 50, so that a chamfer 18 is produced that is straight in at least one direction. If said straight cutting edges 51 are formed on the cutting tool 50, a planar chamfer is obtained. However, it is also possible to produce arcuately rounded chamfers 18 that nonetheless extend straight in one direction, namely when the cutting edges 56 of the cutting tool 50 have a corresponding curvature.

If, alternatively or in addition, chamfers 18 are to be cut that extend in an arc shape about the axis of rotation of the bristle field 10, the bristle support 7 with the bent-away bristle groups and/or the bending or spreading tool 53 holding the same is turned about the axis of rotation of the bristle support 7, while the bent-away bristles are cut.

Once the bristle tufts 11 are chamfered in the desired manner, the aforedescribed groove-shaped depression 16 is cut in the central region of the bristle field 10. For this purpose, a cutting tool 50 that is contoured appropriately convexly on the circumferential side thereof is moved through the bristle field 10 or over the working surface thereof or, conversely, the brush head is moved relative to the cutting tool 50 in a corresponding manner. While doing so, said lateral outer bristle tufts 11 that are intended to protrude in height beyond the edges of the groove-shaped depression 16 are bent away to the side, so that the same are moved out of the region of engagement of the cutting contour for the groove-shaped depression 16.

After the tuft end contours have been cut, the bristles are rounded, for example using a suitable grinding tool. In a refinement of the invention, the bristles of the trimmed bristle tufts 11 are first rounded in an intermediate step after the chamfers 18 have been cut, before the groove-shaped depression 16 is cut. Once the latter is cut, the center bristle tufts in the region of the cut depression 16 are rounded. Alternatively, it is also possible to first cut both the outer bristle tufts 11 and the center bristle tufts or consecutively in the manner already described, before the cut bristle tufts 11 and 13 are then rounded at the bristle ends thereof in a finishing step, as will be explained further below.

FIG. 9 shows a further procedure for producing the brush head and the bristle field thereof shown in FIGS. 1 to 5. Like in the embodiment according to FIG. 8, first all of the bristle tufts are anchored to the bristle support 7 in a suitable manner, whereupon all of the bristle tufts are cut to an even level, as is shown in FIG. 9 (a). The even cutting can be carried out in such a way that the longer, outwardly situated bristle tufts 11 are given the height desired.

According to FIG. 9 (b), the outer bristle tufts 11 are then provided with the chamfers 18, which can be carried out by simultaneous cutting of the outer tufts 11. Cutting the chamfers 18 can be carried out without the aforedescribed bending away of said bristle tufts 11, in particular when the chamfers 18 are inclined merely slightly, and therefore the aforedescribed problem of the bristles being cut too pointed does not arise. Alternatively, however, cutting the chamfers 18 can also take place in the aforedescribed bent-away trimming position.

In order to cut the groove-shaped depression 16 into the central section of the bristle field, said longer outer bristle tufts 11 that have been provided with the chamfers 18 are then bent away according to FIG. 9 (c), so as to have free access to the bristle tufts of the central bristle field section that is to be cut in a groove-shaped manner.

With the longer outer bristle tufts 11 in the bent-away position, the groove-shaped depression 16 is then cut into the bristle field section of the inner bristle tufts 13; see FIG. 9 (d). This can be done as illustrated in FIG. 10. In particular, the bristle tufts 13 can be cut flat once more, as shown in FIG. 10 (b), the flat cut being performed at the height that corresponds to the highest contour sections of the depression 16 to be introduced. In this way, asymmetry of the depression when introducing the same can be prevented, which otherwise occasionally occurs.

After the bristle tufts 13 have been cut flat in this preparatory step, the depression 16 is introduced in multiple process steps, as is shown in FIG. 10 (c). To this end, a plurality of rotating cutting tools having differing diameters and differing directions of rotation are used, each of which is moved through the bristle field in the direction of the longitudinal extension of the depression 16 with the cutting tool rotating. This longitudinal movement can be generated by moving the cutting tool, but also by moving the brush head relative to the cutting tool.

As is shown in FIG. 10 (c), a first cutting tool 50a having a larger radius R1 is used first, which, according to the illustration in FIG. 10 (c), rotates in clockwise direction. After a kind of preliminary depression has been cut into the bristle field section formed by the bristle tufts 13 using this first cutting tool 50a, the depression 16 is re-cut using a second cutting tool 50b, said second cutting tool 50b having a radius R2 greater than that of the first cutting tool 50a and rotating in the opposite direction. In the illustration according to FIG. 10 (c), the second cutting tool 50b rotates in the counter-clockwise direction.

The depression 16 can optionally be re-cut again using a further cutting tool, which may have the same radius as the aforementioned second cutting tool 50b. However, an opposite direction of rotation is used once again for the third cutting pass, see FIG. 10 (c).

Once the groove-shaped depression 16 has been introduced, processing can continue with the subsequent processing steps as shown in FIGS. 9 (e) and 9 (f). In particular, rounding of the cut bristle ends can be performed.

FIG. 9 (e) shows a grinding tool in the form of a grinding roll 70 that is driven in a rotatory manner about the symmetry axis or axis of rotation 71 thereof and is aligned relative to the bristle field such that the bristle ends to be rounded come into engagement with the circumferential side of the grinding roll 70.

In addition to said rotation about the axis of rotation 71, the grinding roll 70 is also moved translationally in a plane that is defined by the axes x and y and that is parallel to the axis of rotation 71 and/or parallel to the surface contour of the bristle field, for example by means of a back and forth movement along the axis x and/or along the axis y; see FIG. 9 (e). Alternatively or in addition to such a translational additional movement, the grinding roll 70 can also be turned about an axis z perpendicular to the axis of rotation 71 thereof, said axis of rotation z being selected to be substantially parallel to the longitudinal extension of the bristles to be rounded.

Alternatively or in addition to the grinding roll 71 shown in FIG. 9 (*e*), it is also possible to use a grinding wheel 60, as is shown in FIG. 9 (*f*), for rounding the bristle ends. This grinding wheel 60 is likewise driven in a rotatory manner about the symmetry axis or axis of rotation 61 thereof, wherein the bristle ends to be rounded can be moved into engagement with the flat end face and/or circumferential side of the grinding wheel 60. The grinding wheel 60 is likewise subjected an additional movement or is moved in an additional movement, in addition to the rotational motion thereof about the axis of rotation; more specifically, in a plane that is defined by the axes x and y in FIG. 9 (*f*) and that is substantially perpendicular to the axis of rotation 61 of the grinding wheel 60. The grinding wheel 60 is aligned or positioned such that the axis of rotation 61 extends substantially parallel to the longitudinal axis of the bristles to be rounded.

Said additional movement in the plane xy can be of a translational nature, for example in the form of back and forth movements along the axis x and/or along the axis y. Alternatively or in addition, the grinding wheel 60 can also be moved along an orbit 62 about the axis of rotation 61 of the grinding wheel; see FIG. 9 (*f*).

Said additional movements of the grinding tools allow the bristle ends to be rounded more evenly. In lieu of the movements of the grinding roll or wheel, said additional movements can also be generated by moving the bristle field in a corresponding manner.

After the bristle ends have been rounded, the laterally bent-away bristle tufts 11, which have been provided with the chamfers 18, can be realigned into the desired position thereof by means of a guiding and/or centering device, as is shown in FIG. 9 (*g*). In particular, said guiding and/or centering device 80 can have a funnel-shaped inlet that captures the bent-away bristle tufts 11, while a downstream centering region can substantially correspond to the outer contour of the bristle field, in order to suitably align the bristle tufts 11; see FIG. 9 (*g*).

According to FIG. 9 (*h*), the bristle tufts 13 can then be covered or separated or moved aside in the central region of the bristle field, so as to be able to round the longer outer bristle tufts 11 at the ends. As is shown in FIG. 9 (*i*), a suitable grinding tool, for example in the form of a grinding roll 70, can be used for this purpose, using suitable movements, as explained; however, alternatively or additionally a grinding wheel 60 can be used as well, using the movements previously explained.

The rounding of the bristle ends of the longer bristle tufts 11 having the chamfers 18 can optionally also be carried out in respect of the center bristle tufts without the covering or separating step shown in FIG. 9 (*h*), wherein the rounding or grinding operation on the bristle tufts 11 can be performed already prior to the aligning step according to FIG. 9 (*g*).

According to FIG. 9 (*j*), the finished bristle field is removed from the processing device and cleaned, which can optionally take place before and/or after the removal from the cutting and rounding device.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention

What is claimed is:

1. A method for producing a brush head of a toothbrush, the method comprising the steps of:
    a) providing bristle tufts that are fixed to a bristle support forming a bristle field of a brush head;
    b) cutting the bristle tufts at their free ends such that a tuft end contour is generated by bending away at least in part at least one bristle tuft and holding the at least one bristle tuft in a bent away position while the tuft end contour of the at least one bristle tuft of a second bristle tuft is cut; and
    c) cutting a depression having a groove-shaped bottom in a central section of the bristle field of the brush head, the depression being arcuately curved in one direction and straight in a direction perpendicular thereto, the groove-shaped depression being cut by:
        i) a first cutting tool having a first diameter and a first direction of rotation, the bristle support being moved in the direction of a longitudinal extension of the bottom of the groove-shaped depression relative to the first cutting tool or the first cutting tool being moved in the direction of a longitudinal extension of the bottom of the groove-shaped depression relative to the bristle field; and
        ii) a second cutting tool having a second diameter different than the first diameter, and a second direction of rotation opposite the first direction of rotation, the bristle support being moved in the direction of a longitudinal extension of the bottom of the groove-shaped depression relative to the second cutting tool or the second cutting tool being moved in the direction of a longitudinal extension of the bottom of the groove-shaped depression relative to the bristle field.

2. The method of claim 1, wherein the tuft end contour is cut by means of a rotating cutting tool, with the circumferential side of which the brush head with the free end of the at least one bristle tuft is moved into engagement.

3. A method according to claim 1, wherein the at least one bristle tuft, or at least a portion thereof, is held in the bent-away trimming position during the cutting operation by means of a bending device having at least one knife-shaped claw, plate-shaped engaging claw, form-fit holding means, friction-fit holding means, or a combination thereof for holding the bristle tuft in place.

4. A method according to claim 1, wherein the at least one bristle tuft that is bent away has a greater length and/or a free end that is situated higher than an adjacent bristle tuft.

5. A method according to claim 1, wherein the at least one bristle tuft is provided at the free end thereof with a chamfer while the bristle tuft is held at least with the bristle portion to be chamfered in a bent-away trimming position.

6. The method according to claim 5, wherein, during cutting of the chamfer at the free end of the bent-away bristle tuft or at the bent-away portion thereof, an angular face is cut at an angle of inclination that is smaller than the angle of inclination of the chamfer of the non-bent bristle tuft.

7. The method according to claim 6, wherein the angle of inclination during cutting of the chamfer relative to the desired angle of inclination of the chamfer of the non-bent bristle tuft is smaller by a difference corresponding approximately to the bending angle by which the bristle tuft, or a portion thereof, is bent away from the neutral position of the bristle tuft, and/or wherein the bending angle is selected approximately corresponding to the angular difference by which the desired angle of inclination of the chamfer of the non-bent bristle tuft is greater than the desired angle of inclination during cutting of the chamfer.

8. The method according to claim 6, wherein the chamfer is cut by means of a cutting edge of the rotating cutting tool, wherein the angle of inclination of the flank of the rotating cutting tool relative to a perpendicular onto the axis of rotation of the cutting tool is smaller than the angle of inclination of the chamfer of the bristle tuft.

9. The method according to the claim 8, wherein a chamfer having an angle of inclination of 30° to 60° relative to a perpendicular of the longitudinal axis of the bristle tuft and/or relative to the bristle support surface is cut on the at least one bristle tuft by means of a rotating cutting tool having a cutting flank positioned relative to a perpendicular onto the axis of rotation of the cutting tool at an angle of inclination of 20° to 40°.

10. A method according to claim 5, wherein the bristle group to be chamfered is bent away to the side on which the chamfer is located on the respective bristle tuft.

11. A method according to claim 1, wherein two bristle tufts which are situated on mutually opposing sides of a bristle field of the brush head and which with the free ends thereof define an elongated working contour, are each provided with a chamfer, wherein when cutting the chamfer the two bristle tufts are each spread apart by means of a knife-shaped or plate-shaped bending or spreading tool, wherein the two bristle tufts are simultaneously provided with the chamfers and are held for this purpose against the circumferential side of the rotating cutting tool, which has two cutting flanks positioned toward one another in a V shape.

12. A method according to claim 2, wherein the cutting tool is moved substantially perpendicularly to the axis of rotation of the cutting tool relative to the brush head for generating a straight chamfer or contour, and/or the brush head is moved in the longitudinal direction of the straight chamfer or contour relative to the rotating cutting tool, and/or wherein the bristle support is turned along with the bristle tuft to be chamfered about a bristle support axis of rotation for generating an arcuately curved chamfer or contour, while the chamfer or contour is cut by means of the rotating cutting tool.

13. The method according to claim 1, wherein the depression and/or another contour in the bristle field is cut in multiple passes using rotating cutting tools having differing radii, wherein a preliminary depression being cut using a cutting tool having a larger radius, before the depression is cut in another pass using another cutting tool having a smaller radius.

14. A method according to claim 1, wherein prior to cutting the depression, the section of the bristle field into which a central depression will be introduced is cut flat and/or level at the height at which the bristle ends of the longest and/or highest bristles of the desired depression are situated.

15. A method according to claim 14, wherein at least one bristle tuft situated along the edge of the bristle field is spread apart and/or bent away from a central section of the bristle field during cutting of a groove-shaped depression.

16. A method according to claim 1, wherein the bristles of the cut bristle tufts are rounded at the bristle ends after the tuft end contour has been cut.

17. The method according to claim 16, wherein the bristle ends are rounded using at least one rotating grinding wheel, the bristle ends being moved into engagement with an end face of the grinding wheel and the grinding wheel being moved translationally substantially perpendicular to the axis of rotation of the grinding wheel along an orbit about the axis of rotation, in addition to the rotational motion thereof in a plane.

18. The method according to claim 16, wherein the bristle ends are rounded using a rotating grinding roll, the bristle ends being moved into engagement with a circumferential side of the grinding roll and the grinding roll being moved translationally and/or turned about an axis perpendicular to the plane in addition to the rotational motion thereof in a plane extending parallel to the axis of rotation and/or perpendicular to the longitudinal axis of a bristle tuft to be processed.

19. A method according to claim 1, wherein all of the bristle tufts to be cut are first cut consecutively or simultaneously, before all or at least one of the cut bristle tufts is rounded at the bristle ends.

20. A method according to claim 1, wherein at least one bristle tuft is cut first and then rounded at the bristle ends thereof, before at least one further bristle tuft is cut and then rounded at the bristle ends thereof.

21. A method according to claim 1, wherein only some of the bristle tufts are first anchored to the bristle support and at least one bristle tuft is cut at the free end thereof and/or is rounded at the bristle ends, before at least one other bristle tuft is anchored to the bristle support.

22. The method according to claim 21, wherein the bristle tufts that are shorter or have lower-lying bristle ends are first anchored to the bristle support, cut and/or rounded at the bristle ends, before the bristle tufts that are longer or have higher-lying bristle ends are anchored to the bristle support, cut, and optionally rounded at the bristle ends.

* * * * *